United States Patent
Konkol et al.

[11] Patent Number: 5,466,644
[45] Date of Patent: Nov. 14, 1995

[54] REACTIVATION OF WATER-SOLUBLE HYDROFORMYLATION CATALYSTS

[75] Inventors: Werner Konkol, Oberhausen; Helmut Bahrmann, Hamminkeln; Wolfgang A. Herrmann, Giggenhausen; Christian Kohlpaintner, Stephanskirchen, all of Germany

[73] Assignee: Hoechst Aktiengesellschaft, Germany

[21] Appl. No.: 378,861

[22] Filed: Jan. 19, 1995

Related U.S. Application Data

[63] Continuation of Ser. No. 174,607, Dec. 28, 1993, abandoned, which is a continuation of Ser. No. 960,899, Oct. 14, 1992, abandoned.

[30] Foreign Application Priority Data

Oct. 24, 1991 [DE] Germany .......................... 41 35 050.2

[51] Int. Cl.$^6$ ................................................. B01J 38/62
[52] U.S. Cl. ................... 502/28; 502/22; 502/29; 568/454
[58] Field of Search ................... 502/20, 22, 24, 502/28; 568/454

[56] References Cited

U.S. PATENT DOCUMENTS

| | | | |
|---|---|---|---|
| 4,248,802 | 2/1981 | Kuhtz ............................ | 568/454 |
| 4,283,304 | 8/1981 | Bryant et al. .................. | 502/24 |
| 4,297,239 | 10/1981 | Bryant et al. .................. | 203/72 |
| 4,374,276 | 2/1983 | Bryant et al. .................. | 568/454 |
| 4,399,312 | 8/1983 | Russell et al. .................. | 568/454 |
| 4,528,404 | 7/1985 | Oswald et al. .................. | 568/454 |
| 4,605,780 | 8/1986 | Billig et al. .................... | 585/848 |
| 4,710,587 | 12/1987 | Bryant et al. .................. | 568/454 |
| 4,801,754 | 1/1989 | Bach et al. ..................... | 568/454 |
| 5,091,350 | 2/1992 | Cokhils et al. ................. | 502/24 |

FOREIGN PATENT DOCUMENTS

| | | | |
|---|---|---|---|
| 19296 | 11/1980 | European Pat. Off. .......... | C07F 9/50 |
| 357997 | 3/1990 | European Pat. Off. .......... | B01J 31/40 |
| 2489308 | 3/1982 | France ........................... | C07C 47/02 |
| 2092907 | 8/1982 | United Kingdom ............. | B01J 31/40 |

*Primary Examiner*—Anthony Mc Farlane
*Attorney, Agent, or Firm*—Jordan B. Bierman; Bierman and Muserlian

[57] ABSTRACT

A process for regenerating a water-soluble hydroformylation catalyst system comprising a coupler rhodium hydrogen-carbonyl complex of rhodium and compounds of the formula

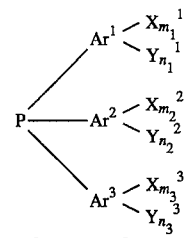

wherein $Ar^1$ and $Ar^2$ and $Ar^3$ are individually phenyl or naphthyl, $Y^1$, $Y^2$ and $Y^3$ are individually selected from the group consisting of alkyl and alkoxy of 1 to 4 carbon atoms, halogen, —OH, —CN, —NO$_2$ and $R^1R^2N$—, $R^1$ and $R^2$ are individually alkyl of 1 to 4 carbon atoms, $X^1$, $X^2$ and $X^3$ are individually carboxylate (—COO$^-$) or sulfonate (—SO$_3^-$), $m_1$, $m_2$ and $m_3$ are individually integers of 0 to 3, at least one of $m_1$, $m_2$ or $m_3$ being equal to or greater than 1, and $n_1$, $n_2$ and $n_3$ are individually integers of 0 to 5 and if appropriate in excess comprising adding maleic acid, fumaric acid or olefinically unsaturated compounds of formula

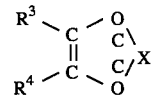

wherein X is selected from the group consisting of O, S, —

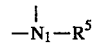

or

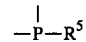

and $R^3$, $R^4$ and $R^5$ are individually hydrogen, or alkyl or aryl to an aqueous solution of the catalyst system in an amount sufficient to remove sulfonated or carboxylated alkylarylphosphanes.

10 Claims, No Drawings

REACTIVATION OF WATER-SOLUBLE HYDROFORMYLATION CATALYSTS

This application is a continuation of application Ser. No. 08/174,607 filed Dec. 28, 1993, now abandoned, which is a Continuation of application Ser. No. 07/960,899, filed Oct. 14, 1992, now abandoned.

STATE OF THE ART

It is known that the reaction of olefins with carbon monoxide and hydrogen (hydroformylation) results in aldehydes and alcohols which contain one carbon atom more than the starting olefin. The reaction is catalyzed by hydridometal carbonyls, preferably those of the metals of Group VIII of the Periodic Table. In addition to cobalt which is widely used in industry as the catalyst metal, rhodium has increasingly gained importance recently. In contrast to cobalt, rhodium allows the reaction to be carried out under a low pressure. Moreover, n-aldehydes are preferentially formed, and isoaldehydes are formed to only a minor extent from straight-chain terminal olefins. Finally, the hydrogenation of the olefins to saturated hydrocarbons is also significantly lower in the presence of rhodium catalysts than when cobalt catalysts are used.

In the processes known in the ark, the rhodium catalyst is a hydridorhodium carbonyl modified by additional ligands, preferably tertiary organic phosphines or phosphites. The ligands are usually present in excess so that the catalyst system comprises the complex compound and free ligand. The use of such rhodium catalysts permits the hydroformylation reaction to be carried out at pressures below 30 MPa.

However, removal of the reaction products and recovery of the catalysts dissolved homogeneously in the reaction product cause difficulties in this process. In general, the reaction product is distilled off from the reaction mixture for this purpose. In practice, because of the heat sensitivity of the aldehydes and alcohols formed, this path can be taken only for hydroformylation of lower olefins, i.e. olefins having up to about 8 carbon atoms in the molecule. Moreover, it has been found that exposure of the distillation material to heat also leads to considerable catalyst losses due to decomposition of the rhodium complex compounds.

The deficiencies described are avoided by using catalyst systems which are soluble in water and such catalysts are described, for example, in DE-PS 26 27 354. The solubility of the rhodium complex compounds is achieved here by using sulfonated triarylphosphines as a constituent of the complex. In this process variant, when the reaction has ended, the catalyst is separated off from the reaction product simply by decanting the aqueous and organic phase, i.e. without distillation and therefore without additional process steps with heat. Another feature of this procedure is that n-aldehydes are formed with a high selectivity from straight-chain terminal olefins, and iso-aldehydes are formed to only a quite minor extent. Sulfonated, and in addition also, as is known, for example, from DE-A1 31 35 127, carboxylated triarylphosphines are preferably employed as complex constituents of water-soluble rhodium complex compounds.

During a continuous procedure or during repeated use of the same catalyst solution, the activity of the catalyst system decreases over the course of time as does its ability to form unbranched aldehydes with a high selectivity. This loss in activity and selectivity is due to various reasons. The causes include catalyst poisons such as iron carbonyl which forms due to the action of synthesis gas on the transportation lines or the reactor material, or also higher-boiling condensation products which are formed from the aldehydes. The decrease in the ratio of phosphine to rhodium during more prolonged use of the catalyst system also has a selectivity-reducing effect, this decrease being the consequence of degradation and oxidation processes to which the sulfonated or carboxylated phosphines are subjected. In the course of these reactions, for example, phosphine oxides, phosphine sulfides, aromatic sulfonic acids, α-hydroxybutyldisulfophenylphosphine oxide, disulfophosphinous acid and disulfophenylphosphinic acid, in each case in the form of their salts, are formed from the sulfonated compounds.

Neither phosphine oxides and phosphine sulfides nor the salts of aromatic sulfonic acids and of disulfophenylphosphinic acid have a catalytic action by themselves or together with rhodium. The same also applies to cluster compounds of rhodium, which can form from the catalytically active rhodium complex compounds after long reaction times. To regenerate the original activity and selectivity of the catalyst system, the catalyst constituents which have become inactive can be replaced without removing them from the reaction mixture by fresh rhodium compound and/or fresh phosphine until the initial concentration is established.

Finally, sulfonated or carboxylated alkyl-arylphosphines which have an inhibiting effect on the hydroformylation reaction should also be mentioned as conversion products. In the course of the reaction of the olefins with carbon monoxide and hydrogen, these mixed aliphatic-aromatic phosphines form from the sulfonated or carboxylated triarylphosphines by replacement of aryl radicals by alkyl groups, the alkyl groups deriving from the olefin which is being hydroformylated. Thus, for example, in the reaction of propylene in the presence of sulfonated or carboxylated triphenylphosphine, disulfonated or dicarboxylated n-propyl-diphenylphosphine is formed. The mixed aliphatic-aromatic phosphines give catalytically inactive complex compounds with rhodium, with the consequence that the rate of reaction and catalyst activity decrease significantly.

OBJECTS OF THE INVENTION

It is an object of the invention to provide a novel process for regenerating a water-soluble hydroformylation catalyst system by selective removal of inactivating alkyl arylphosphines therefrom.

This and other objects and advantages of the invention will become obvious from the following detailed description.

THE INVENTION

The novel process of the invention for regenerating a water-soluble hydroformylation catalyst system comprising a coupler of rhodium and compounds of the formula

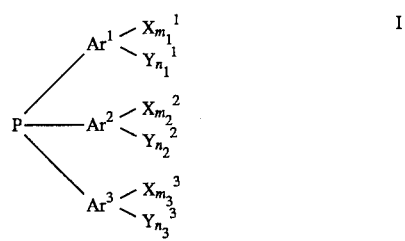

wherein $Ar^1$ and $Ar^2$ and $Ar^3$ are individually phenyl or naphthyl $Y^1$, $Y^2$ and $Y^3$ are individually selected from the group consisting of alkyl and alkoxy of 1 to 4 carbon atoms, halogen, —OH, —CN, —NO₂ and R¹R²N—, R¹ and R² are individually alkyl of 1 to 4 carbon atoms, , X¹, X² and X³ are individually carboxylate (—COO⁻) or sulfonate (—SO₃⁻), $m_1$, $m_2$ and $m_3$ are individually integers of 0 to 3, at least one of $m_1$, $m_2$ or $m_3$ being equal to or greater than 1, and $n_1$, $n_2$ and $n_3$ are individually integers of 0 to 5 and if appropriate in excess comprises adding maleic acid, fumaric acid or olefinically unsaturated compounds of formula

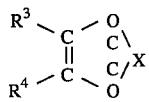
II wherein X is selected from the group consisting of O, S, —

or

and R³, R⁴ and R⁵ are individually hydrogen, or alkyl or aryl to an aqueous solution of the catalyst system in an amount sufficient to remove sulfonated or carboxylated alkyl-arylphosphines.

Surprisingly, the process leads to a significant revival, even of those catalysts which have been used for relatively long periods of time. The activity and selectivity in many cases acquire their original values again by the measure of the invention. It should be emphasized in particular that reactivation of the catalyst can take place during its use, so that it is not necessary to separate off the catalyst solution from the reaction mixture or to interrupt the running synthesis. Moreover, the conversion products of the water-soluble alkyl-arylphosphines and the water-soluble olefinic compounds can remain in the aqueous solution. The novel procedure in this way differs advantageously from the hydroformylation in a homogeneous phase using rhodium/arylphosphine catalysts.

Undesirable conversion products of the lipophilic arylphosphines can also be rendered harmless in this variant of the oxo process by reaction with certain olefinically unsaturated compounds (cf. EP 00 19 296 A1). However, it is necessary to remove the conversion products from the reaction mixture by extraction with water. A prerequisite of this process is thus the removal of the catalyst system from the reaction mixture, and it therefore cannot be carried out in an operating plant.

An unexpected side effect of the procedure of the invention is the increase in the rate of reaction during hydroformylation of higher olefins, i.e. olefins having 9 or more carbon atoms, using catalyst solutions comprising compounds originating from the reaction of water-soluble alkyl-arylphosphines with water-soluble olefinically unsaturated compounds. The newly formed compounds are possibly phase transfer reagents (solubilizing agents), which improve the solubility of the higher olefins in the aqueous phase and thus accelerate the reaction.

The aqueous catalyst solutions used in the synthesis are usually used for regeneration of catalyst systems by the process of the invention. As a rule, they comprise rhodium in concentrations of 450 to 800 ppm by weight and water-soluble phosphines in concentrations of 25 to 30% by weight, in each case based on the aqueous solution. The rhodium is present in the form of a carbonyl-hydrogen compound which additionally contains phosphine bonded as a complex. Non-bonded phosphines are dissolved in the solution as salts, preferably alkali metal, ammonium or quaternary ammonium salts and they correspond to formula I above.

Phosphines in which Ar¹, Ar₂ and Ar³ are identical and are phenyl or naphthyl, X¹, X² and X³ are a carboxylate (—COO⁻) or a sulfonate (—SO₃⁻), $m_1$, $m_2$ and $m_3$ are each 0 or 1, with the proviso that the sum of $m_1$, $m_2$ and $m_3$ is at least 1 and $n_1$, $n_2$ and $n_3$ are 0, are preferably employed. Examples of such phosphines are tri (m-sulfophenyl)-phosphine, phenyl-di (m-sulfophenyl)-phosphine and diphenyl-(m-sulfophenyl) -phosphine. In addition, the solution contains the other conversion products of phosphines characterized in more detail above, for example phosphine oxides and phosphine sulfides, and if appropriate also other substances such as solubilizing agents. The formation of by-products takes place regardless of the individual olefinically unsaturated compounds which have been hydroformylated under the action of the aqueous catalyst solution.

The alkyl-arylphosphines recognized as troublesome are compounds which contain one or two alkyls and 2 or 1 sulfonated or carboxylated aryl groups. These phosphines are also capable of forming complex compounds with rhodium, but it has been found that they have only little or no catalytic action. The inactivity of the alkylarylphosphines is possibly based on their higher basicity compared with arylphosphines. In accordance with the assumed mode of formation, the aryls in the mixed aliphatic-aromatic phosphines coincide with those which are contained in the triarylphosphines of the catalyst system, and the number of carbon atoms in the alkyl is the same as the number of carbon atoms in the olefin employed. Thus, for example, propyl-di(m-sulfophenyl)phosphine and dipropyl-(m-sulfophenyl)phosphine are formed during hydroformylation of propylene in the presence of tri(m-sulfophenyl)phosphine, and phosphines which contain, in addition to one or two m-sulfophenyl groups, two or one butyl group, are formed during hydroformylation of butene.

To render the alkyl-arylphosphines contained in the catalyst solution harmless, they are reacted with olefinic compounds of the formula

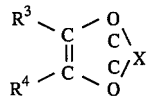
II wherein X is O, S, N—R⁵ or P—R⁵; R³, R⁴ and R⁵ are individually alkyl or aryl. Preferably, R³, R⁴ and R⁵ are hydrogen, unbranched or branched C₂–C₆-alkyls or unsubstituted or substituted phenyls.

It is not necessary for the olefinic compounds to be readily soluble in water. It is sufficient for them to pass into the aqueous phase, even in only a small amount, and to pass into this phase again at the rate at which they are consumed by the reaction. Nevertheless, substances which are readily soluble in water and sparingly soluble or insoluble in organic media are preferred to simplify and accelerate the reaction and to avoid enrichment of the olefinically unsaturated compounds in the organic phase.

Olefinically unsaturated compounds which have proven to be suitable are maleic acid, fumaric acid, maleic anhydride and maleimide, maleic acid and maleic anhydride being particularly suitable. The compounds are used as such or, inter alia to simplify their metering, as solutions, advantageously in water or in solvents which are water-miscible. The concentration of the olefinically unsaturated compounds in the solutions can be varied within wide limits, and solutions which comprise 0.1 to 40% by weight, preferably 0.1 to 10% by weight of unsaturated compound (based on the solution) are preferred.

The reaction takes place in a simple manner by mixing the catalyst phase and olefinically unsaturated compound and the temperature and pressure are not critical for the reaction. The reaction is generally carried out at temperatures of from 0° to 150° C., temperatures of 100° C. and more of course requiring the use of increased pressure. The reaction can be carried out particularly easily under the conditions of the hydroformylation reaction and in parallel with this in the same reactor. The alkyl-arylphosphine and olefinic compound react with one another in a molar ratio of 1:1. Accordingly, at least one mole of olefinically unsaturated compound must be used per mole of phosphine to be removed, the amount of which can be determined analytically, for example by HPLC analysis. The olefinically unsaturated compound is advantageously used in excess, and there is no critical upper limit, although it is advisable to use 15 to 20 moles of olefinically unsaturated compound per mole of alkyl-arylphosphine.

The reactivation of the catalyst system can also be repeated. Both in the case where the olefinically unsaturated compound is used in excess and in the case of repeated reactivation of the catalyst solution, it should be remembered that the reaction of the water-soluble alkyl-arylphosphine does not take place selectively, but that sulfonated or carboxylated triarylphosphine always also reacts to a minor extent at the same time. It may therefore be necessary to top up the sulfonated or carboxylated triarylphosphine in the catalyst solution from time to time to maintain the optimum ratio of rhodium to phosphine.

In the following examples, there are described several preferred embodiments to illustrate the invention. However, it should be understood that the invention is not intended to be limited to the specific embodiments.

The following abbreviations are used:

PDSPP: di-Na-propyldisulfophenylphosphine

TPPDS: di-Na-phenyldisulfophenylphosphine

TPPTS: tri-Na-phenyltrisulfophenylphosphine

MA: maleic anhydride

Experimental procedure:

The experiments were carried out in a continuously operating laboratory apparatus comprising a stirred reactor, a phase separator and a product receiver with waste gas regulation. The reactor was filled with 150 ml and the phase separator with 130 ml of catalyst solution. The catalyst solution contained about 300 ppm by weight of rhodium, and the molar ratio of phosphorus (III)/Rhodium varied between 100:1 (fresh catalyst solution) and 15:1 (spent catalyst solution). After the reaction conditions had been established, i.e. reactor temperature of 122° C. and synthesis gas pressure of 5.0 MPa ($CO:H_2$=1:1), 20–40 g of propylene were pumped continuously into the reactor depending on the activity of the catalyst solution employed.

The reaction mixture overflowing into the phase separator (aqueous-organic product, $CO/H_2$, propylene) was separated and the aqueous catalyst solution settling out was recycled continuously into the reactor. Crude oxo product and synthesis gas were separated from one another in the product receiver, and the aqueous solution obtained was pumped into the reactor in a closed circuit. The crude aldehyde issuing from the reaction was collected in the product receiver, and its amount was determined hourly.

The parameters of "activity" and "productivity" defined below were determined to describe the activity of the particular catalyst solutions.

$$\text{Activity:} \frac{\text{mole of } (n+i) - \text{aldehyde}}{\text{g atom of rhodium} \times \text{minute}}$$

$$\text{Productivity:} \frac{\text{g of } (n+i) - \text{aldehyde}}{\text{cm}^3 \text{ of catalyst solution} \times \text{hour}}$$

For this, the amount of crude aldehyde obtained in the product receiver was measured hourly, and the amount of catalyst in the reactor was measured at the end of the experiment.

EXAMPLES 1–3 (TABLE 1)

Examples 1–3 show the deactivating action of PDSPP on a fresh Rh/TPPTS catalyst solution used in the hydroformylation. Example 1 is a reference experiment with fresh catalyst solution and its (absolute) activity is 15.8, and is set at 100 as the relative activity. In Examples 2 and 3, increasing amounts of PDSPP were added to the catalyst solution and the molar ratio of (TPPTS+TPPDS)/PDSPP served as an orientation parameter.

TABLE 1

|  | Example | | |
|---|---|---|---|
|  | 1<br>Na-TPPTS | 2<br>Addition of<br>1.73 mol %<br>of PDSPP | 3<br>Addition of<br>7.4 mol % of<br>PDSPP |
| A value | 15.78 | 14.5 | 7.33 |
| P value | 0.213 | 0.202 | 0.101 |
| P(III)/Rh ratio | 100 | 100 | 100 |
| (TPPTS + TPPDS):<br>PDSPP | 252:0 | 240.7:1.4 =<br>172:1 | 225.4:10.2 =<br>22:1 |
| Relative activity | 100 | 92 | 46 |

On addition of 1.7 mole %, based on the P(III) content, of PDSPP, still no influence was found in the context of the range of variation. On increasing the amount to 4.7 mole %, this corresponded to a molar ratio of (TPPTS+TPPDS)/PDSPP of 22:1, but a clear, highly adverse influence was detected.

EXAMPLES 4 AND 5 (TABLE 2)

Example 4, as the reference experiment, shows the A and P values of an aged catalyst solution. The relative activity had fallen to 41% and the molar ratio of (TPPTS+TPPDS)/PDSPP is 13:1.

Example 5 illustrates the effect of the addition of maleic anhydride as the olefinically unsaturated compound of the invention and the relative activity rose again to 77.5%.

TABLE 2

|  | Example | |
|---|---|---|
|  | 4<br>Aged contact | 5<br>Aged contact<br>+ 0.4% by weight<br>of MA |
| A value | 6.51 | 11.3 |
| P value | 0.092 | 0.165 |
| P/Rh ratio | 32 | 17 |

TABLE 2-continued

|  | Example | |
|---|---|---|
|  | 4 Aged contact | 5 Aged contact + 0.4% by weight of MA |
| (TPPTS + TPPDS)/PDSPP | 94:7.4 = 13:1 | 59.5:1.6 = 37:1 |
| Relative activity | 41.2 | 77.5 |

EXAMPLES 6–11 (TABLE 3)

To determine optimum values, the addition of maleic acid was varied between 0.05 and 0.5% by weight based on the aged catalyst solution in Examples 7 to 11. For this, in each case the amount of MA shown in Table 3 was added to 350 g of aged catalyst solution in a 1-liter stirred flask under a nitrogen atmosphere, and the mixture was heated at reflux for 2 hours and then was analyzed by HPLC analysis.

TABLE 3

| Optimization of the addition of MA to the aged catalyst solution | | | | | |
|---|---|---|---|---|---|
| Example | 7 | 8 | 9 | 10 | 11 |
| MA addition % by weight | — | 0.05 | 0.10 | 0.4 | 0.5 |
| mmol of (TPPDS + TPPDS) | 88.5 | 87.0 | 76.7 | 59.9 | 47.7 |
| mmol of PDSPP | 5.2 | 4.2 | 1.8 | 1.6 | 2.4 |
| $\frac{TPPTS + TPPDS}{PDSPP}$ | 17.02 | 20.71 | 42.6 | 37.4 | 19.9 |

Example 7 shows the amount of TPPTS and TPPDS and of PDSPP (in each case in mmol) in the catalyst solution. The molar ratio of (TPPTS+TPPDS)/PDSPP again served as an optimization parameter and the higher the value of the quotient, the greater the selective degradation of the undesirable PDSPP. As can be seen, the optimum was an addition of 0.1% by weight of MA. The following examples were therefore carried out with this amount added.

EXAMPLES 12–13 (TABLE 4)

|  | Example | | |
|---|---|---|---|
|  | 4 Aged catalyst | 12 Aged catalyst + 0.1% by weight of MA | 13 Aged catalyst + 0.1% by weight of MA + 7% by weight of TPPTS |
| A value | 6.5 | 16.9 | 21.9 |
| P value | 0.092 | 0.256 | 0.335 |
| P/Rh ratio | 32 | 17 | ~25 |
| (TPPTS + TPPDS)/PDSPP | 13:1 | 28:1 | not calc. |
| Relative activity (%) | 41.2 | 107 | 139 |

As Example 12 shows, it was possible to increase the activity again to the starting level of a fresh catalyst solution, in the context of the range of variation, although the total salt concentration (by this is understood all the salts contained in the solution) of the catalyst solution had since risen from 15 to about 30%.

Example 13 illustrates that the activity can be raised far above the starting level by increasing the P(III) content with fresh TPPTS. The relative activity rose to 139%. To explain this surprising phenomenon, it is assumed that the degradation products contained in the aged catalyst solution and the phosphonium salts formed by maleic acid have solubilizing properties, but these can only display their action when the activity-reducing Rh/PDSPP complexes have been largely degraded.

Various modifications of the process may be made without departing from the spirit or scope thereof and it is to be understood that the invention is intended to be limited only as defined in the appended claims.

What we claim is:

1. A process for regenerating a water-soluble hydroformylation catalyst system in a hydroformylation reaction system, said reaction system comprising an aqueous phase, containing said catalyst system, and an organic phase, containing an olefin, said catalyst system comprising a rhodium, hydrogencarbonyl complex of rhodium and compounds of Formula I

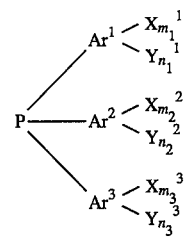

wherein $Ar^1$, $Ar^2$, and $Ar^3$ individually represent phenyl or naphthyl, $Y^1$, $Y^2$, and $Y^3$ individually represent a substituent selected from the group consisting of alkyl and alkoxy of 1 to 4 carbon atoms, halogen, —OH, —CN, —$NO_2$ and $R^1R^2N$—, in which $R^1$ and $R^2$ individually represent alkyl of 1 to 4 carbon atoms $X^1$, $X^2$, and $X^3$ individually represent carboxylate (—$COO^-$) or sulfonate (—$SO_3^-$), $m_1$, $m_2$, and $m_3$ individually represent integers of 0 to 3, at least one of $m_1$, $m_2$, or $m_3$ being equal to or greater than 1, and $n_1$, $n_2$, and $n_3$ individually represent integers of 0 to 5, said regeneration being achieved by adding at least one compound selected from the group consisting of maleic acid, fumaric acid, and olefinically unsaturated compounds of Formula II

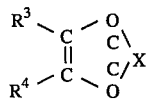

wherein X is selected from the group consisting of O, S, —$N_1$—$R^5$ or —P—$R^5$, $R^3$, $R^4$, and $R^5$ individually representing hydrogen, alkyl, or aryl, to said aqueous phase in an amount sufficient to permit removal of sulfonated or carboxylated alkyl-arylphosphanes, whereby said catalyst system is regenerated without having to remove said reaction products from said aqueous phase.

2. The process of claim 1 wherein at least one mole of olefinically unsaturated compound is added per mole of sulfonated or carboxylated alkyl arylphosphine contained in the catalyst system.

3. The process of claim 1 wherein 15 to 20 moles of olefinically unsaturated compound are added per mole of sulfonated or carboxylated alkyl arylphosphine contained in the catalyst system.

4. The process of claim 1 wherein the olefinically unsaturated compound is maleic anhydride or maleic acid.

5. The process of claim 1 wherein the olefinically unsaturated compound is maleimide.

6. The process of claim 1 wherein the olefinically unsaturated compound is fumaric acid.

7. The process of claim 1 wherein the olefinically unsaturated compound is added to the catalyst system as an aqueous solution.

8. The process of claim 7 wherein the aqueous solution contains 0.1 to 40% by weight of the olefinically unsaturated compound based on the solution in dissolved form.

9. The process of claim 7 wherein the aqueous solution contains 0.1 to 10% by weight of the olefinically unsaturated compound based on the solution in dissolved form.

10. The process of claim 1 wherein said compounds are added in stoichiometric excess.

* * * * *